(12) United States Patent
Eichele et al.

(10) Patent No.: US 6,623,701 B1
(45) Date of Patent: Sep. 23, 2003

(54) SPECIMEN CHAMBER FOR THE LIQUID TREATMENT OF BIOLOGICAL SPECIMENS

(75) Inventors: Gregor Eichele, Hannover (DE); Uwe Herzig, Hannover (DE)

(73) Assignee: Max-Planck-Gesellschaft zur Forderung der Wissenschaften e.V., Munich (DE)

(*) Notice: Subject to any disclaimer, the term of this patent is extended or adjusted under 35 U.S.C. 154(b) by 179 days.

(21) Appl. No.: 09/644,465

(22) Filed: Aug. 23, 2000

(30) Foreign Application Priority Data

Sep. 2, 1999 (DE) .......................... 199 41 905

(51) Int. Cl.[7] .................................................. B01L 3/00
(52) U.S. Cl. .................... 422/102; 422/99; 422/104; 435/283.1; 435/288.3; 435/288.5; 436/174; 436/180
(58) Field of Search .............................. 422/58, 63, 64, 422/65, 99, 102, 104, 68.1; 436/43, 46, 47, 174, 180; 435/283.1, 287.2, 287.8, 288.3, 288.5; 356/335, 336, 337, 338, 244, 246

(56) References Cited

U.S. PATENT DOCUMENTS

| | | | | |
|---|---|---|---|---|
| 2,942,520 A | * | 6/1960 | Rose | 88/40 |
| 4,596,695 A | | 6/1986 | Cottingham | 422/58 |
| 4,790,640 A | | 12/1988 | Nason | 350/534 |
| 5,066,465 A | * | 11/1991 | Kano et al. | 422/58 |
| 5,192,503 A | * | 3/1993 | McGrath et al. | 422/57 |
| 5,364,790 A | * | 11/1994 | Atwood et al. | 435/288 |
| 5,527,510 A | * | 6/1996 | Atwood et al. | 422/104 |
| 5,665,599 A | * | 9/1997 | Minuth | 435/288.3 |
| 5,675,700 A | * | 10/1997 | Atwood et al. | 392/382 |
| 5,830,413 A | | 11/1998 | Lang et al. | 422/100 |
| 5,958,760 A | * | 9/1999 | Freeman | 435/286.5 |
| 6,358,475 B1 | * | 3/2002 | Berndt | 422/100 |

FOREIGN PATENT DOCUMENTS

| | | |
|---|---|---|
| DE | 297 21 359 | 3/1998 |
| EP | 0 310 399 | 4/1989 |
| EP | 0 366 241 | 5/1990 |

* cited by examiner

*Primary Examiner*—Jill Warden
*Assistant Examiner*—Dwayne R Handy
(74) *Attorney, Agent, or Firm*—Nields & Lemack

(57) ABSTRACT

A specimen chamber (10) for the liquid treatment of at least one specimen (90) comprises a base plate (20) and a carrier plate (30), between which a gap-formed accommodation space is formed for the specimen, whereby the base plate and carrier plate (20, 30) are held together with a clamping device (60) in a frame arrangement (50), and in order to form the accommodation chamber are separated from one another by spacer elements (40), and the base plate (20) features, at an intake (11) on the side pointing towards the carrier plate (30), a tapering shape in order to form a wedge-shaped liquid reservoir (21).

12 Claims, 4 Drawing Sheets

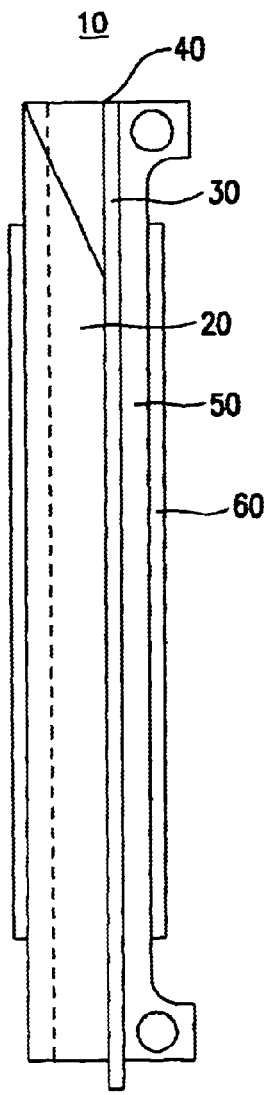
FIG. 2
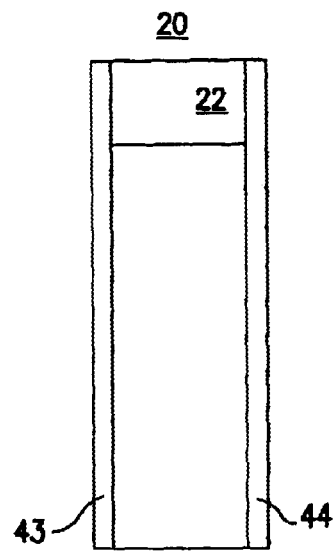
FIG. 3
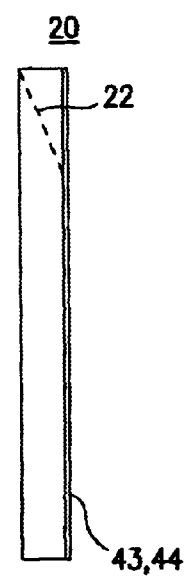
FIG. 4
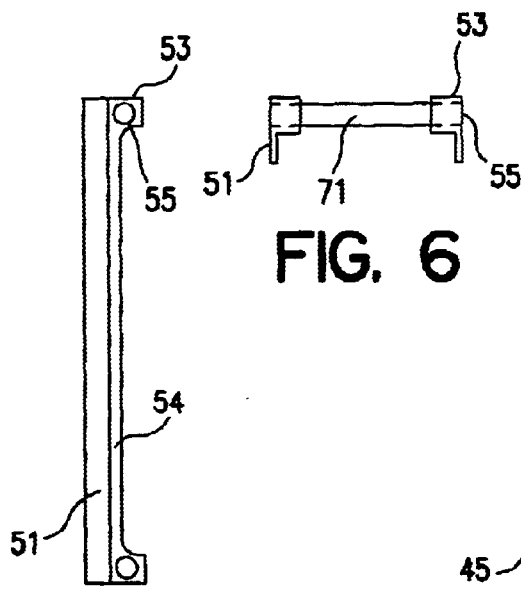
FIG. 5
FIG. 6
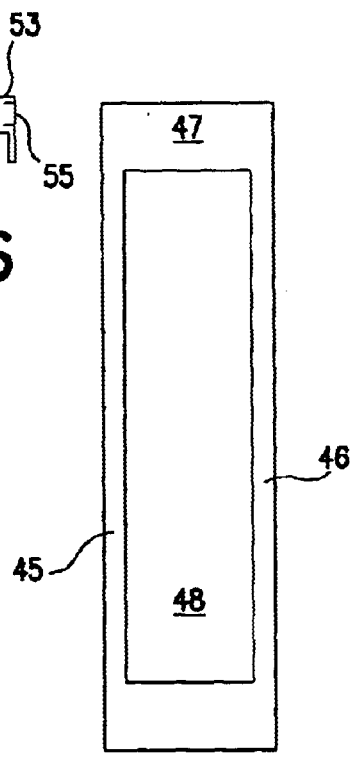
FIG. 7

SPECIMEN CHAMBER FOR THE LIQUID TREATMENT OF BIOLOGICAL SPECIMENS

FIELD OF THE INVENTION

The invention relates to a specimen chamber for the liquid treatment of at least one specimen, in particular a throughflow chamber, for the liquid treatment of biological specimens, such as, for example, a throughflow chamber for detecting the presence of nucleic acids and proteins by means of gensonde hybridisation or by means of antibodies.

PRIOR ART

Genomes of animals and plants contain genes in the order of size of $10^5$, which are expressed in a specific manner. Knowledge of the gene expression in the tissues which form an organism is of fundamental significance in the understanding of the physiology and patho-physiology of a living being. Interest pertains in the expression analysis in individual biological cells. This is achieved by in-situ hybridisation (hereinafter ISH), in combination with immune histochemical processes. In addition to this, in this connection the hybridisation and representation of DNA microarrays is also of interest.

The term ISH is understood to mean the hybridisation of the genomic DNA or DNA generated by RT-PCR, or RNA synthesised in vitro, and, on the other hand, the hybridisation of cellular mRNA. From the principle of ISH, which is today generally described in text books, and which was first described by M. L. Pardue, a process has now developed which is carried out in laboratories all over the world, with a large number of manually-performed individual stages. Major factors of the process are nucleic acid hybrid formation and the evidencing of the hybrids. For the formation of hybrids, the specimens, which include sections of tissue with plant or animal cells, are subjected to liquid reagents under precisely controlled temperature conditions and in accordance with predetermined time programmes. An ISH may comprise 50 individual stages, for example, in which situation, at each individual stage, the tissue specimen must, within a few seconds, be brought to a predetermined temperature in the range from, for example, 4° C. to 100° C. with a precision of ±1° C., and subjected to predetermined reagents. Both with regard to the time expenditure and with regard to the precision of the performance of the process, the manual procedure used hitherto is no longer suited to the demands for the processing of large numbers of specimens ("high throughput" processes), which may involve hundreds or even thousands of prepared specimens.

With the aim of automating the ISH, throughflow chambers have been developed which are designed to contain tissue specimens or microarrays and carry out their liquid processing. An example of a conventional throughflow chamber 10', which is marketed by the company of Shandon Southern Instruments Ltd., Great Britain, is illustrated in FIG. 12 (prior art). The throughflow chamber 10' is based essentially on a combination of a cover plate arrangement 20' and a carrier plate 30', in which situation the cover plate arrangement 20' features on its intake side a hopper-shaped extension 21' to take in the processing liquids. A tissue specimen is placed in the space between the cover plate arrangement 20' and the carrier plate 30', and fixed in position there. The combination of the cover plate arrangement 20' and the carrier plate 30' is located in a cassette (not shown). For the liquid processing, the individual reagents are introduced via the extension 21'. Although the throughflow chamber 10' allows for automatic use using pipetting robots, it suffers from the following disadvantages, which excludes its use for the ISH described heretofore, or restricts it to specific and less demanding process protocols.

Due to the complicated structure of the chamber sections with the outer cassette, temperature of the conventional throughflow chamber cannot be controlled in a reproducable manner. In addition to this, with the conventional throughflow chamber according to FIG. 12, the cover plate arrangement 20' consists of a plastic which is not form-resistant if used at temperatures above 60° C. which occur during ISH. Accordingly, the reproducibility of the reagent throughflow is limited. In addition, the design of the cover plate arrangement 20' and the chemical composition of the cover plate renders impossible the uniform flow of the solutions containing formamide, used in the ISH, with the result that a spatially inhomogeneous hybridisation reaction arises, in which, for example, air bubbles occur or tissue particles or specimens float around. The combination of plastic with glass materials, too, for the formation of the chamber walls, excludes the possibility of reproducible temperature control.

In general, none of the generally known specimen or throughflow chambers are suitable for the analysis of DNA microarrays, in particular with processes with high throughput. Even if the specimen chambers for tissue specimens used hitherto in the laboratory sector has been capable of thermostatic adjustment, automatic reagent exchange is impossible. The manual loading of specimens with manual pipettes, however, is unsuitable for processes with high throughput.

SUMMARY OF INVENTION

The object of the invention is to provide an improved specimen chamber for liquid treatment of specimens, of which the temperature control is reliable and reproducible, and which will be form-resistant even at repeated temperature adjustment, and which, in particular, will allow for automatic process treatment in the throughflow principle even at high specimen throughput (about 100 to 500 per passage).

The basic idea of the invention particularly consists of the provision of a specimen chamber consisting of a base plate and a carrier plate, which are separated from one another by a predetermined interval by spacer elements, and are held together by means of a frame arrangement. The base and carrier plates have, for preference, the same surface area. In the assembled state they form an aligned packing unit, as a result of which the interval between the plates forms a receptacle or accommodation for the specimen. Given the design of the specimen chamber as a throughflow chamber, the accommodation (cutout) is open to two mutually opposed sides for the formation of an intake or an outlet, and closed to the other sides in a fluid-tight manner. To achieve this, the spacer elements run in strip form between the two edges of the base plate and carrier plate, aligned relative to one another, between the intake and the outlet. The base plate tapers at the intake (the thickness of the plate is reduced towards the end of the plate), to form a reservoir between the base plate and the carrier plate.

In the frame arrangement, the base plate and the carrier plate are held together aligned to one another. To provide for mutual fixation of the plates in the frame arrangement, provision is made for a clamp device, which on the one hand encompasses the frame arrangement, and, on the other, encompasses the plates arranged in it, creating a uniform compression tension. Under the effect of the compression tension, the cutout formed between the base plate and the carrier plate for the specimen is closed laterally along the spacer element, in a liquid-tight manner. The frame arrangement is also equipped with a hang-up device, which is designed to bring the throughflow chamber to a contact platform of a temperature control device.

The base and carrier plates of the specimen chamber according to the invention consist for preference of the same material, or of similar materials with regard to their thermal properties. This improves the temperature control, avoids deformations, and also causes the flow properties of the treatment liquids flowing through to be uniform at the taking of the specimen. The plates are for preference made of glass or, depending on the application, of a temperature-resistant plastic or quartz glass.

A subject of the invention is also a temperature adjustment device (referred to as a thermoblock) with a large number of temperature-adjustable contact platforms arranged in rows and gaps. The contact platforms in the operating state have an almost vertical (e.g. 15°) setting, or a setting pivoted further away from the vertical by a predetermined angle (up to almost 90°), in which situation a profiled projection is provided at the upper end to accommodate the specimen chamber according to the invention. The projection interacts with the hang-up device of the specimen chamber in such a way that, in the suspended state, the specimen chamber is drawn because of its weight towards the contact platform and establishes good thermal contact with it.

The invention has the following advantages. The specimen chamber according to the invention is particularly well-suited for use as a throughflow chamber for the liquid treatment of biological specimens. The chamber has an especially simple modular design with essentially only two elements (the base plate and the carrier plate), which are clamped in the frame. The glass structure is resistant to the reagents used in each case, in particular against aqueous and organic solvents. The parts of the throughflow chamber, which can be easily separated without further ado by releasing the clamping device are, on the one hand, easily and rapidly assembled after the carrier plate has been loaded with a specimen, and can be separated from one another without further ado after the processing of the specimen in order for the specimen to be removed and for the cleaning of the chamber. The throughflow chamber is capable of being treated in an autoclave, which is of advantage for reuse.

The compact design, exercising pressure tension by means of the clamping device, ensures optimum heat conduction from an outside temperature regulating device to the specimen in the throughflow chamber. The base and carrier plates, made of glass, do not undergo any deformation at all in the temperature ranges of interest, below 100° C. The throughflow chamber can be rapidly located on the contact platform of a thermoplatform in a reproducible manner. At the same time, the frame arrangement of the chamber is constructed in such a way that the specimen remains accessible for visual observation and optical measurements.

A particularly important advantage is obtained if the carrier plate is formed by a standardised glass object carrier, such as is known from optical microscopy. The throughflow chamber according to the invention is thus rendered entirely compatible with the usual manipulation techniques for glass object carriers. In addition, the carrier plate can be designed with a substrate suitable for follow-on measurements or also for additional handling procedures. If the carrier plate consists, for example, of UV transmitting glass of optically high quality, the synthesis of oligonucleotides is made possible by masked photochemical reactions directly on the carrier plate.

The throughflow chamber according to the invention is characterised by substantially improved flow properties of the reagents thanks to the accommodation arrangement for the specimens. While, for example, in a conventional throughflow chamber according to FIG. 12 the processing liquid comes in contact with plastic on the one hand and with glass on the other, with the result that differences in the flow rates occur on both sides of the chamber, and therefore flow inhomogeneities or even bubbles form, with the throughflow chamber according to the invention the reagents which pass through encounter the same surface resistance on all the chamber walls, with the result that flow inhomogeneities or bubbles are avoided.

The use of the throughflow chamber according to the invention is not restricted to the ISH, but can be applied in general to any specimens desired, and biological specimens in particular, which are to be processed with liquid reagents, such as specimens for the examination of antibody reactions, for the hybridisation and representation of DNA microarrays, or similar functions.

BRIEF DESCRIPTION OF THE DRAWINGS

Further details and advantages of the invention can be derived from the description of the appended drawings. These show.

The invention is described hereinafter without restriction with regard to the specimen chamber, which is designed as a throughflow chamber. Implementation as a closed reaction chamber is by analogy also possible.

Figure 1:
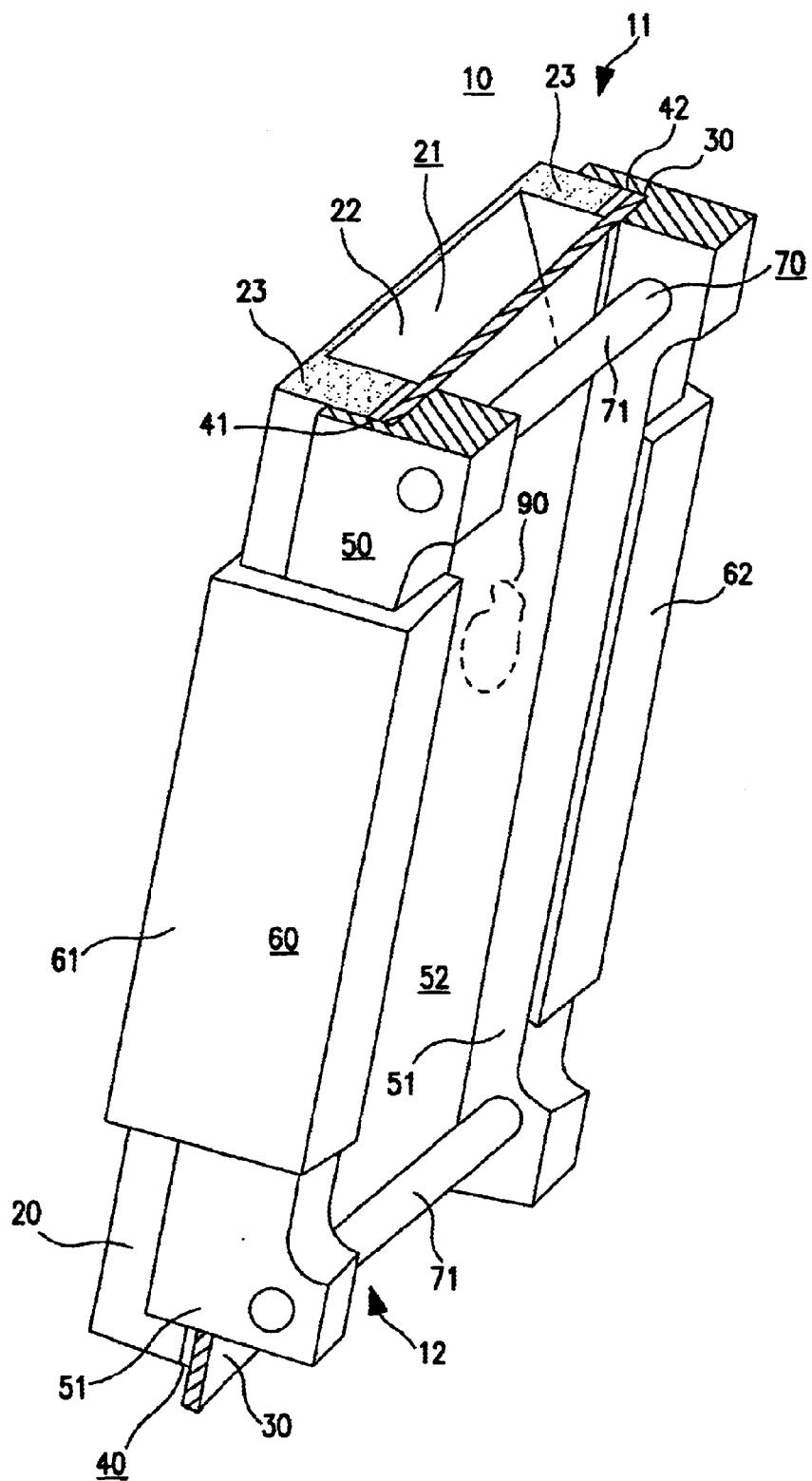
FIG. 1 A schematic perspective representation of a first embodiment of the specimen chamber according to the invention, FIG. 2 A sectional view of the specimen chamber shown in FIG. 1, FIGS. 3, 4 Plan and side views of a base plate of a modified specimen chamber, FIGS. 5, 6 Side views of a frame arrangement of a specimen chamber according to FIG. 2, FIG. 7 An illustration of a film spacer element, FIG. 8 A schematic sectional representation of a thermoblock according to the invention, FIG. 9 An enlarged representation of contact platforms of a thermoblock according to FIG. 8, FIG. 10 An illustration of the location of a specimen chamber according to the invention, in accordance with FIG. 2, on a contact platform according to FIG. 9, FIG. 11 A schematic perspective representation of a gripper for specimen chambers according to the invention, and FIG. 12 A schematic perspective view of a conventional throughflow chamber (prior art).

FIG. 1 illustrates a preferred embodiment of the invention in a perspective representation, as basic components of the throughflow chamber 10, the base plate 20, the carrier plate 30, the spacer element 40, the frame arrangement 50, the clamping device 60, and the hang-up device 70. In the assembled state, the base plates and carrier plates 20, 30, together with the spacers 40, form an aligned packing unit in the frame arrangement 50, whereby this packing unit is held together by the clamping device 60. In the operational state, the throughflow chamber 10 is arranged almost vertically, as shown, in which situation an intake 11 is arranged at the upper end and an outlet 12 at the lower end. At the intake 11 or outlet 12 the throughflow chamber 10 is open to the top or bottom for the intake and discharge of the processing liquids. In FIG. 2 these basic components of the throughflow chamber 10 are illustrated in a sectional representation.

The base plate 20 is a glass plate with a rectangular base and a predetermined thickness. Typical dimensions in interaction with an object carrier as the carrier plate are, for example, 73 mm×26 mm×6 mm. With the use of a conventional cover glass, or a cover glass of the type used in microscopy as the carrier plate, the surface area of the base plate is selected as correspondingly small. At one end, which in the operational state forms the intake 11, the base plate 20 is designed to be inclined obliquely in the centre so as to form a liquid reservoir 21, so that a wedge-shaped ramp is formed between two webs 23. The webs 23 have a width of, for example, about 3 mm. The liquid reservoir 21 is delimited by the ramp area 22, inasmuch as the thickness of the glass plate 20 is reduced towards its end, and by the lateral webs 23, at which the thickness of the glass plate 20 is retained as far as the end. In an alternative embodiment of the base plate according to FIGS. 3 and 4, the lateral delimitation is effected by webs of the spacer element 40 (see below).

From the side of the carrier plate 30, the liquid reservoir 21 is delimited by the carrier plate 30 itself. The ramp area 22 has for preference a sufficient size for the liquid reservoir 21 to feature a volume of about 0.2 to 1 ml. The volume of the liquid reservoir 21 is for preference a multiple of the volume of the accommodation area (about 120 μl) formed between the base plate and the carrier plate 20, 30. This has the following advantage: On the one hand, processing reagents can be reliably accommodated in the liquid reservoir, which are expensive and need only be introduced in a volume corresponding to the accommodation space for the specimen. On the other hand, with larger volumes, the washing or rinsing reagents required, which may be less expensive, can be introduced in correspondingly larger quantities in one single loading process. Depending on the use, therefore, provision can be made for the volume of the liquid reservoir 21 to be enlarged still further beyond the example value given. To do this, provision may be made for a greater thickness of the base plate 20.

The carrier plate 30 is likewise a glass plate, which for preference corresponds in shape and size to standardised object carriers or cover glasses, such as are known from optical microscopy. The carrier plate 30 is likewise provided with a modifying layer (not shown) on the side pointing towards the base plate 20. The modifying layer, such as is known from microscopy, forms covalent links between the polar silicate of the carrier plate 30 and the tissue specimen 90 which is to be held, so that said specimen is fixed on the carrier plate 30. The tissue sample 90 is, for example, a section of tissue with a thickness in the range from 1 μm to 50 μm.

Due to the spacer element 40, an accommodation space in the form of a gap or layer shape for the specimen 90 is formed between the flat surfaces facing one another of the base plate and carrier plate 20, 30. The spacer elements 40, according to the first embodiment shown in FIG. 1, comprise two spacer strips 41, 42, which are arranged running from the intake 11 to the outlet 12, on the surfaces facing one another of the base plate and carrier plate 20, 30, on the lateral edges. The spacer strips 41, 42, consist of a plastic material which is capable of being compressed under the effect of the compression tension of the clamping device 60, and is liquid-tight in the compressed state. The spacer strips 41, 42, in each case consist, for example, of a strip about 2 to 3 mm wide made of silicone rubber with a predetermined thickness, which is applied before the chamber is assembled onto the base plate or carrier plate. Due to the fact that the transverse dimension of the specimen accommodation space between the base plate and the carrier plate 20, 30, is determined by the spacer strips 41, 42, the thickness of the strip is selected depending on the application. For ISH applications, for example, it amounts to about 100 to 130 μm. The strip of silicone rubber serves to advantage simultaneously as a spacer element between the base plate 20 and the carrier plate 30 placed on it (object carrier with specimen 90), and, because of its properties, also serves to provide lateral sealing of the chamber. Due to the formation of a space between the plates, the risk is prevented of specimen material (e.g. thick tissue material) from being undesirably compressed. In addition to this, the inflow of processing liquids (reagents) to the material which is to be treated is also made easier.

According to a related embodiment of a throughflow chamber according to the invention, the spacer elements 40 comprise two lateral epoxy webs 43, 44, polymerised onto the base plate 20, which are illustrated in FIGS. 3 and 4. In these figures, only the base plate 20 is shown in a plan view and side view respectively. By distinction from the embodiment according to FIG. 1, the ramp area 22 at the upper end of the base plate 20 is formed without lateral webs. The wedge-shaped ramp runs across the entire width of the plate. The lateral delimitation of the liquid reservoir 21 is provided in this case by the continuous epoxy webs 43, 44. The epoxy webs 43, 44, project on the side of the glass plate 20 which points towards the carrier plate 30, i.e. on the side with the ramp area 22, above the surface of the glass plate 20, so that in turn a step is formed as a spacer element in relation to the carrier plate 30. To do this, the epoxy webs 43, 44, which are polymerised in place, are milled off at the desired height above the glass upper edge (e.g. 100 to 130 μm).

The epoxy webs 43, 44, polymerised in place according to FIG. 3 may, as a substitute, also be replaced by plastic strips (e.g. of PTFE) of the same shape and size, which in the inserted state are pressed in the frame arrangement 50 (see FIG. 1) laterally against the glass plate 20, and project above the surface of the glass plate 20 on the side pointing towards the carrier plate 30. The lateral PTFE strips in turn form a projection in relation to the surface of the glass plate 20, corresponding to the desired distance between the glass plate and the carrier plate 20, 30 (e.g. in the range from 100 to 130 μm).

According to a further option illustrated in FIG. 7, the spacer elements 40 are formed by film strips 45, 46, on the base plate and the carrier plate 20, 30. The film strips 45, 46, consist for example of PE film or another film material conventionally used in the laboratory sector, which is resistant to the processing liquids used. Provision is made for a broad strip 47 to be prepared with one or more sequential "O"-shaped cut-outs 48, so that, when laid on the base plate or carrier plate 20, 30, it runs straight at the edge of the plate on the surface pointing towards the other plate in each case. The cut-out 48 has a length extension (e.g. 80 mm) which is greater than the length of the base plate and carrier plate, and a transverse extension (e.g. 16 mm) corresponding to the desired distance between the spacer elements. As a result of this, the lateral film strips 45, 46, are formed (with a width of, for example, 5 mm). Before the throughflow chamber is assembled, the O-shaped film with a cut-out 48 is simply laid on the plate concerned, and compressed between the plates in connection with the frame arrangement 50 under the effect of the clamping device 60. The parts of the broad strip 47 which project at the narrow ends of the packing unit are cut off, so that only the narrow film strips 45, 46, remain between the plates. This arrangement has the advantage that a cheap disposable product is crated with the spacer element, which, if required, can even be reproduced without further ado in the laboratory by stamping the strip 47.

A further optional form of the spacer element, not shown, is based on the use of a solvent-resistant paint, which is applied in strips on one or both of the mutually opposed plate surfaces, or a plastic coating such as is used for the formation of lettering fields on substrates, made, for example, of the material "Superfrost" (registered trademark).

The spacer elements can also be formed by strip-shaped projections of the plate edges, provided with a seal.

The frame arrangement 50 has a double function. On the one hand it serves to align the base plate and carrier plate 20, 30, in relation to one another and, on the other, it serves to handle the throughflow chamber 10, e.g. in relation to its suspension in a temperature control device. According to FIG. 1, the frame arrangement 50 consists of two profiled side cheek elements 51 and two connecting bars which are formed by the bars 71 of the hang-up device. Between the bars 71 a space or a free area 52 is formed, which allows for the direct contact of the contact platforms of the thermoblock (see below) on the outer surface of the carrier plate 30. The frame arrangement is made of a plastic material (e.g. PON) or metal (e.g. aluminium or stainless steel). The dimensions of the frame arrangement 50 are adapted to the design and size of the base plate and carrier plate 20, 30. Accordingly, the space between the side cheek elements 51 corresponds essentially to the surface area of the carrier plate 30. With the embodiments described above, with spacer elements in the form of lateral webs polymerised or pressed into place, this space is widened accordingly. The longitudinal extension of the side cheek elements 51 corresponding to the vertical flow direction can extend in part or in full over the length of the base plate and carrier plate 20, 30, as is illustrated in FIGS. 1 and 2 respectively. The free surface 52 also forms a window, which serves to provide visual and/or technical measurement observation of the specimen 90 in the throughflow chamber 10.

The side cheek elements 51 extend over the entire length of the frame arrangement 50. They are of such a height that the spacer element 40 and the plate located at a distance from the base surface 52 (in this case the base plate 20) are covered at least in part.

At least one hang-up device 70 is provided for on the frame arrangement 50. The hang-up device 70 is in general formed by means of a hook, a projection, or a loop or similar element, whereby the throughflow chamber, or other releasable containers, can be suspended. For preference, however, the hang-up device 70 is formed, as illustrated, by at least one of the bars 71 of the frame arrangement 50, which extends between two lateral projections 53 at the end of the side cheek elements 51.

For preference, the frame arrangement 50 is equipped at its ends with two hang-up devices 70. The frame arrangement 50 has webs 54 running along the side cheek elements over their entire length, which widen at their ends to form the projections 53. Located in each of the projections 53 is a drillhole 55 for accommodating a bar 71 for the individual hang-up device 70.

The clamping device 60 comprises at least two laterally located U-shaped clamps, which tension together the packing unit formed of the base plate and carrier plate 20, 30, with the spacer elements 40 and the frame arrangement 50. According to the embodiment shown, a continuous clamp 61, 62, is provided for on each side of the throughflow chamber 10. The clamps are made of a suitable spring-effect plastic material or metal.

Figure 8:
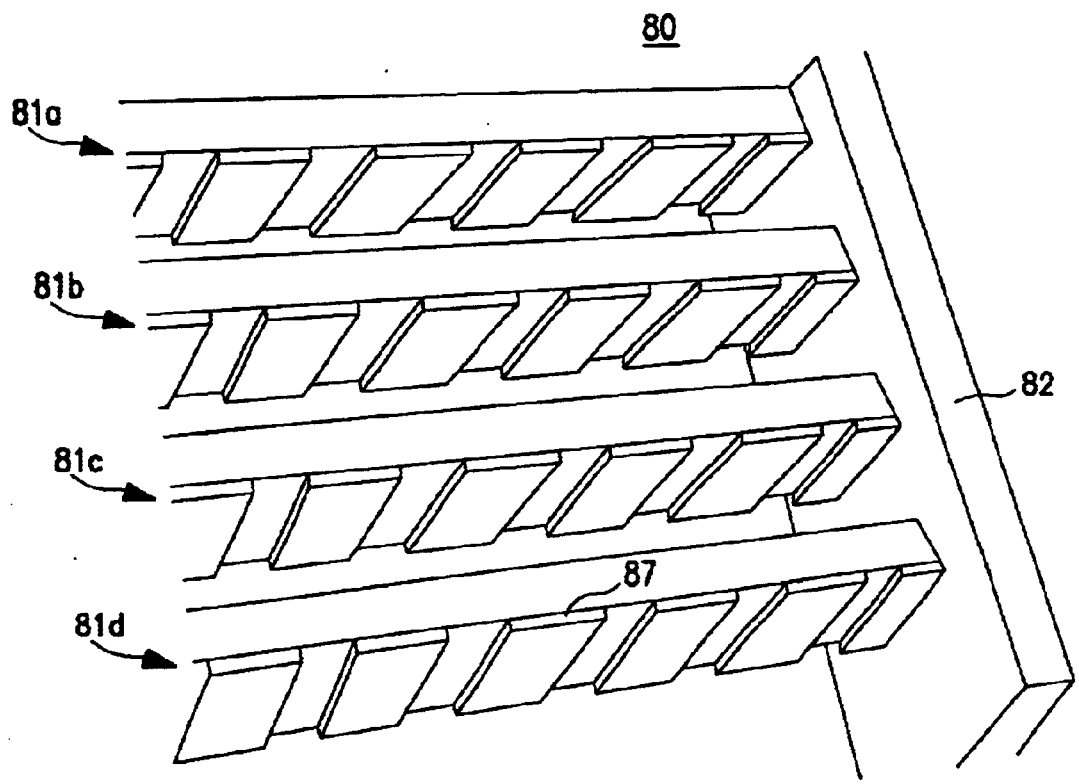
Figure 9:
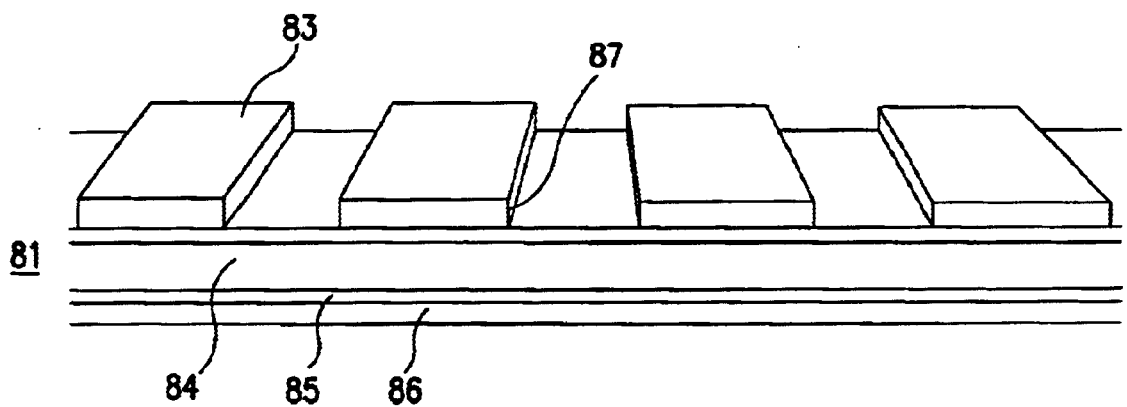
Figure 10:
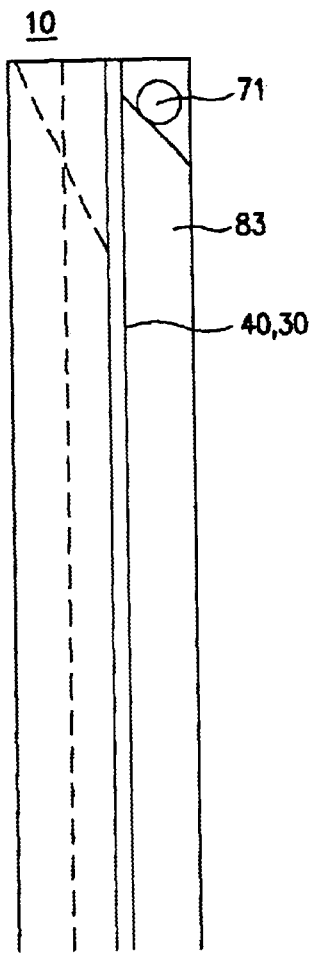
Figure 12:
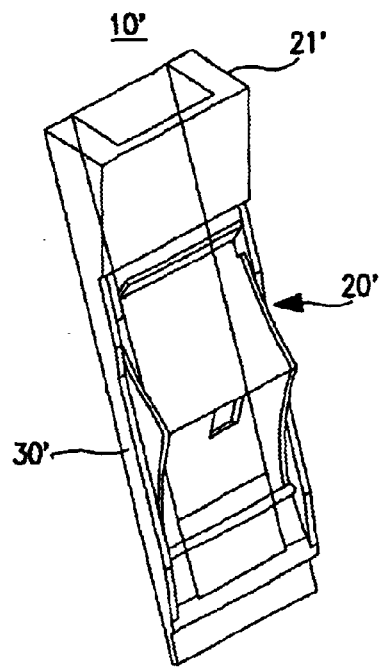

FIGS. 8 to 10 illustrate the interaction of the throughflow chamber according to the invention with a temperature control device in the form of a thermoblock 80.

The thermoblock 80 comprises at least one carrier row 81, 81a, 81b, 81c, 81d, each of which is located at a side wall 82 of the thermoblock 80. Each carrier row 81 (see FIG. 8) features a large number of contact platforms 83, which are located in a contact plate 84. The contact plate 84 is connected via a seal 85 with a cover plate 86. The contact plate 84 has an inner milled cut-out, so that a cavity is formed towards the cover plate 86. The cavity is designed so that a temperature control medium (e.g. water) can flow through the likewise hollow side wall 82. The thermoblock 80 is connected for this purpose to a thermostat device (not shown) for controlling the temperature of the temperature control medium. Emergence through the sides of the temperature control medium is prevented by the seal 85.

The contact plate 84 also has other milled-out cut-outs, by means of which the contact platforms 83 are formed as a single unit with the contact plate 84. Each contact platform 83 has a profiled projection 87 on at least one side, to accommodate the hang-up device 70 of the throughflow chamber described above. The contact plate 84 and the contact platforms 83 consist of a material of high thermal conductivity, for preference of metal, such as aluminium or copper. The cover plate 86 is made, for example, of steel.

The hang-up of a throughflow chamber 10 on a thermoblock 83 is illustrated as a sectional view according to FIG. 10. The throughflow chamber 10 (represented in part) has a structure which corresponds essentially to that illustrated in FIGS. 1 and 2. The contact platform 83 has the profiled projection 87 at its upper end in operating function, in the form of a wedge-shaped oblique element, which engaged behind the bar 71 of the hang-up device 70. The advantage of this arrangement lies in the fact that the throughflow chamber 10 is drawn by its weight and the interaction of the bar 71 with the wedge-shaped oblique element of the projection 87 towards the contact platform 83, with the result that it provides a good heat-conductive contact.

For the operation of the throughflow chambers, the thermoblock 80 is placed in a trough (not shown), which represents a closed liquid accommodation element. The processing liquid which flows through the throughflow chambers is caught in the trough. At the same time, the solutions collected in the trough give off an atmosphere which is at least partially enriched with evaporated solvents, which prevents the undesirable drying of the throughflow chambers. The trough is equipped with a discharge device to draw off parts of the liquids caught in the trough, and a cover device. The cover device serves to close the trough on the top side, and can, if appropriate, be provided with a large number of closable apertures, according to its arrangement, to load the throughflow chambers.

Figure 11:
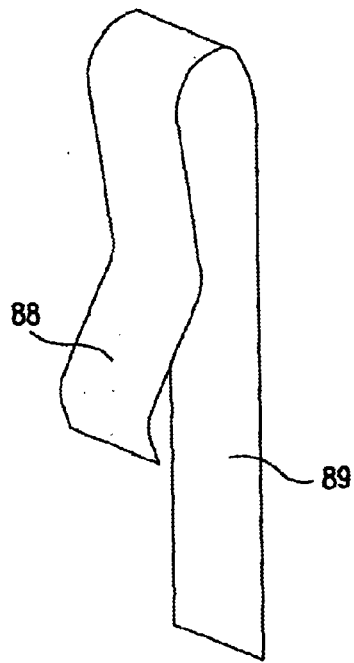

FIG. 11 illustrates a gripper, which is designed for the manual handling of the throughflow chambers in the thermoblock. The gripper has the shape of a bent strip, through which on one side a tongue 88 is drawn, and a cantilever element 89 on the other. The width of the strip is slightly less than the intervals between the projections 53 of the frame arrangement 50, and amounts, for example, to 17 mm. The tongue 88 is shaped at its curved end so as to engage with the bar 71 of the frame arrangement 50. The cantilever element 89 projects in the longitudinal direction of the gripper out beyond the length of the tongue 88, so as to provide a support for the throughflow chamber which has been set in position. The length of the boom 89 amounts to, for example, 80 mm. The gripper consists of a spring-loaded steel plate (thickness about 5 mm).

For the practical use of the throughflow chambers according to the invention, the specimen which is to be examined is first arranged on the carrier plate 30 (e.g. the object carrier). The carrier plate 30 is then brought together with the base plate 20 and inserted into the frame arrangement 50. The total package is then fixed in position with the clamping device 60. Next, the throughflow chamber is suspended by the gripper illustrated in FIG. 11 on a contact platform 83 of the thermoblock 80. The thermoblock 80 is loaded for the high-throughput process with a large number of throughput chambers, each with one of more specimens. Next, for example, the ISH is carried out under precisely controlled temperature conditions in the temperature range between 4° C. and 100° C., according to predetermined time programs. The treatment liquids in each case are introduced from above into the intakes 11 of the throughflow chambers 10. The treatment liquids run through the throughflow chambers, whereby the desired reactions are incurred on the specimens in each case. After the process sequence, and in accordance with a specific substance, time, and temperature control protocol, which is inherently known and therefore is not explained in detail, the throughflow chambers are removed from the thermoblock and conveyed onwards for further examination of the specimens, e.g. optical measurements or microscopic examination.

The throughflow chamber described above is not restricted to the ISH applications, but rather can be applied in the liquid treatments of any desired synthetic or biological specimens in layer form. Depending on the design of the sealed spacer element, it is also possible without further ado to proceed further from the throughflow principle. By sealing the accommodation space between the base plate and carrier plate on the side opposite the intake, a closed reaction chamber is formed. The specimen chamber according to the invention can be modified as a throughflow or reaction chamber, depending on its application, in relation to its size also. A further modification relates to the size and shape of the base plate and carrier plate. These have been described heretofore in reference to the object carrier format. A structure adapted to the format of substrates for DNA microarrays is possible in the corresponding manner. In addition, the plates are described with different thicknesses, whereby the ramp was provided for at the thicker (base) plate. As an alternative, it is also possible for both the base plate and carrier plate to be equipped with ramps, which point towards one another in the assembles state.

What is claimed is:

1. Specimen chamber for the liquid treatment of at least one specimen, with a base plate and a carrier plate, between which a gap-form accommodation space for the specimen is arranged, the base plate and the carrier plate being held together by a clamping device in a frame arrangement, and being separated from one another by spacer elements for the formation of the accommodation space, wherein the frame arrangement comprises two side cheek pieces having first and second ends, each end being connected to the next end of the other side cheek piece by a bar, whereby the side cheek pieces extend over the entire length of the frame arrangement and cover the spacer elements and the base plate at least in part, and whereby at one end and on the side facing to the carrier plate the base plate is progressively reduced in thickness to form a ramp between two webs and thus has an intake with a wedge-shaped liquid reservoir.

2. Specimen chamber according to claim 1, in which the accommodation space is open at the intake and at an outlet which is located at the end of the baseplate opposite to the intake, and the spacer elements are provided as strips between the intake and the outlet at the side edges of the base plate and carrier plate.

3. Specimen chamber according to claim 2, in which the spacer elements are formed by strip-shaped projections at the plate edges, said projections being provided with a seal.

4. Specimen chamber according to claim 2, in which the spacer elements are formed by strips made of compressible plastic material on the plate edges.

5. Specimen chamber according to claim 4, in which the spacer elements are made of silicone rubber, epoxy resin, polyethylene, or PTFE.

6. Specimen chamber according to claim 2, in which the spacer elements are formed by webs from plastic material at the lateral edges of the base plate, which project beyond the surface of the base plate on the side facing to the carrier plate.

7. Specimen chamber according to claim 6, in which the spacer elements are made of silicone rubber, epoxy resin, polyethylene, or PTFE.

8. Specimen chamber according to claim 1, in which the two side cheek pieces being connected by bars providing a hang-up device to the frame arrangement for the suspension of the specimen chamber in a temperature control device.

9. Temperature control device with a large number of temperature-controllable contact platforms arranged in rows and gaps, which in each case have a profiled projection at their upper end for the location of the specimen chambers in accordance with claim 8.

10. Method of performing liquid treatments of specimens in layer form using a specimen chamber with a base plate and a carrier plate, between which a gap-form accommodation space for the specimen is arranged, the base plate and the carrier plate being held together by a clamping device in a frame arrangement, and being separated from one another by spacer elements for the formation of the accommodation space, wherein the frame arrangement comprises two side cheek pieces having first and second ends, each end being connected to the next end of the other side cheek piece by a bar, whereby the side cheek pieces extend over the entire length of the frame arrangement and cover the spacer elements and the base plate at least in part, and whereby at one end and on the side facing to the carrier plate the base plate is progressively reduced in thickness to form a ramp between two webs and has an intake with a wedge-shaped liquid reservoir, said method comprising:

loading said specimens on said carrier plate, inserting said carrier plate and said base plate into said frame arrangement and clamping the assembly with said clamping device, and processing said specimens.

11. Method according to claim 10, wherein the gap-form accommodation space is a throughflow chamber in which at least one specimen is arranged and through which treatment liquids are run through, whereby desired reactions are incurred on the specimen.

12. Method according to claim 11, wherein the temperature of the specimen chamber is controlled in the temperature range between 4° C. and 100° C.

* * * * *